US010780431B1

United States Patent
Hsu et al.

(10) Patent No.: US 10,780,431 B1
(45) Date of Patent: Sep. 22, 2020

(54) METHOD OF USING BIOPOLYMER TO SYNTHESIZE TITANIUM-CONTAINING SILICON OXIDE MATERIAL AND APPLICATIONS THEREOF

(71) Applicant: ORIENTAL UNION CHEMICAL CORP., Taipei (TW)

(72) Inventors: Yu-Chuan Hsu, Kaohsiung (TW); Pin-Hsuan Huang, Taipei (TW); Chien-Chang Chiang, Taipei (TW); Ying-Shih Chang, Taipei (TW); Hsi-Chin Tsai, Kaohsiung (TW); Hong-Ping Lin, Tainan (TW)

(73) Assignee: ORIENTAL UNION CHEMICAL CORP., Taipei (TW)

(*) Notice: Subject to any disclaimer, the term of this patent is extended or adjusted under 35 U.S.C. 154(b) by 0 days.

(21) Appl. No.: 16/361,693

(22) Filed: Mar. 22, 2019

(51) Int. Cl.
*B01J 29/89* (2006.01)
*B01J 37/04* (2006.01)
*B01J 37/00* (2006.01)
*B01J 37/08* (2006.01)
*B01J 35/10* (2006.01)
(Continued)

(52) U.S. Cl.
CPC ............ *B01J 29/89* (2013.01); *B01J 35/1038* (2013.01); *B01J 35/1066* (2013.01); *B01J 35/1071* (2013.01); *B01J 35/1076* (2013.01); *B01J 37/0018* (2013.01); *B01J 37/04* (2013.01); *B01J 37/08* (2013.01); *C01B 37/005* (2013.01); *C07D 303/04* (2013.01); *C01P 2006/14* (2013.01); *C01P 2006/17* (2013.01)

(58) Field of Classification Search
CPC .... B01J 29/89; B01J 35/1038; B01J 35/1066; B01J 35/1071; B01J 35/1076; B01J 37/08; B01J 37/04; B01J 37/005; B01J 37/0018; C07D 303/04; C01B 37/005; C01P 2006/14; C01P 2006/17
USPC ........................................................ 549/529
See application file for complete search history.

(56) References Cited

U.S. PATENT DOCUMENTS

| 688,782 A | 12/1901 | Hillery |
| 3,923,843 A * | 12/1975 | Wulff ..................... B01J 21/063 549/529 |

(Continued)

FOREIGN PATENT DOCUMENTS

CA 2314233 A1 * 9/2000

*Primary Examiner* — Taylor V Oh
(74) *Attorney, Agent, or Firm* — Muncy, Geissler, Olds & Lowe, P.C.

(57) ABSTRACT

A method of using biopolymer to synthesize titanium-containing silicon oxide material and applications thereof are disclosed. The method comprises steps: mixing a titanium source, a silicon source, an acid source, a base source, a biopolymer and a solvent to form an aqueous solution, and letting the aqueous solution react to form a semi-product; performing aging, solid-liquid separation and drying of the semi-product to obtain a dried solid; and performing calcination or extraction of the dried solid to obtain a titanium-containing silicon oxide material with a high specific surface area. The present invention adopts a biopolymer as the templating agent, which makes the fabrication process of titanium-containing silicon oxide material more environment-friendly. After calcination or extraction, the product still has superior catalytic activity, able to catalyze epoxidation of olefins and favorable for the production of epoxide.

14 Claims, 2 Drawing Sheets

(51) Int. Cl.
*C01B 37/00* (2006.01)
*C07D 303/04* (2006.01)

(56) References Cited

U.S. PATENT DOCUMENTS

| | | | | |
|---|---|---|---|---|
| 4,833,260 | A | * | 5/1989 | Neri ..................... B01J 29/035 |
| | | | | 549/531 |
| 6,512,128 | B2 | | 1/2003 | Yamamoto et al. |
| 7,018,950 | B2 | | 3/2006 | Yamamoto |
| 2006/0140843 | A1 | * | 6/2006 | Sung .................... B01J 19/0093 |
| | | | | 423/351 |
| 2009/0234143 | A1 | * | 9/2009 | Yamamoto ............... B01J 21/08 |
| | | | | 549/523 |

* cited by examiner

METHOD OF USING BIOPOLYMER TO SYNTHESIZE TITANIUM-CONTAINING SILICON OXIDE MATERIAL AND APPLICATIONS THEREOF

BACKGROUND OF THE INVENTION

Field of the Invention

The preset invention relates to a method of using a template method to synthesize titanium-containing silicon oxide material and applications thereof, particularly to a method of using biopolymer as the template agent to synthesize titanium-containing silicon oxide material and using the titanium-containing silicon oxide material as a catalyst to directly oxidize olefins into epoxides.

Description of the Related Art

The titanium-containing silicon oxide materials usually have porous structures with high-specific surface area, favorable to function as absorptive agents, catalysts, and catalyst carriers. At present, the synthesis of titanium-containing materials is often realized by hydrothermal processes using surfactants as template agents. It is the most well-known example among them: a positively-charged quaternary ammonium salt surfactant is used as the template agent. U.S. Pat. Nos. 7,018,950, 688,782 and 6,512,128 all disclosed the methods for fabricating titanium-containing silicon oxide catalysts, comprising steps: dissolving a silicon source, a titanium source and a quaternary ammonium salt (functioning as a template agent) in a solvent and agitating them to obtain a solid containing a catalyst and a template agent; and removing the templating agent to obtain a titanium-containing silicon oxide catalyst with a special pore diameters, a pore diameter distribution and a special specific volume ratio. In the template method for fabricating titanium-containing silicon oxide material, titanium is introduced into the silicon dioxide material with a high specific surface area to diversify the catalytic activity of the material. In the fabrication process, the templating agent generates micelles, and the added silicon compound aggregates around the micelles and forms silicon oxide substrates on the micelles. The templating agent (i.e. the surfactant) may be removed by a high-temperature calcination process or an extraction process, whereby is created a material having porous structures whose size and shape is similar to that of the templating agent. The advantages of the fabrication process are that the pore volume of the resultant material can be controlled via modifying the size of the molecules of the templating agent and that the pore size can be controlled via modifying the size of the micelles of the template agent. However, the surfactant, which functions as the template agent, is expensive and likely to generate toxicity and pollute the environment.

In order to overcome the abovementioned problems, the applicant of the present invention has developed a low-cost non-toxic green material as the templating agent for fabricating titanium-containing silicon oxide material to reduce pollution to the environment. Further, the titanium-containing silicon oxide material fabricated by the present invention has high catalytic activity in epoxidation.

SUMMARY OF THE INVENTION

The primary objective of the present invention is to provide a method of using biopolymer to synthesize titanium-containing silicon oxide material and applications thereof, wherein an aqueous solution, which is formulated with a titanium source, a silicon source, an acid source and a base source, a biopolymer and a solvent, is aged, filtered, dried, calcined (or extracted) to obtain a titanium-containing silicon oxide material with a high-specific surface area and a high catalytic activity, which may function as a catalyst to catalyze epoxidation of olefins and generate epoxides.

In order to achieve the abovementioned objective, the present invention proposes a method for fabricating titanium-containing silicon oxide material, wherein an aqueous solution, which is formulated with a titanium source, a silicon source, an acid source and a base source, a biopolymer, and a solvent, is agitated uniformly; next, the aqueous solution is kept at a temperature ranging from −20 to 200° C. and agitated persistently for 0.5-5 hours; next, the aqueous solution is aged at a temperature ranging from 60-200° C. for 6-48 hours; next, a solid-liquid separation process is undertaken; next, the solid obtained in the solid-liquid separation process is dried; next, a calcination process or an extraction process of the dried solid is undertaken to obtain a titanium-containing silicon oxide material with a high specific surface area.

The titanium-containing silicon oxide material fabricated by the present invention meets the following conditions:
1. The average diameter of the pores of the titanium-containing silicon oxide material is greater than 10 Å;
2. The pores with diameters ranging from 5-200 Å have a volume of more than 90% of the total pore volume.
3. The titanium-containing silicon oxide material has a specific pore volume greater than 0.2 $cm^3/g$.

In the method of the present invention, the titanium source may be sourced from titanates, inorganic titanium sources, or combinations thereof. The silicon source may be amorphous silicon dioxide, alkoxysilanes, silicates, or combinations thereof. The acid source may be sourced from any material able to lower the pH value of the system, such as organic acids, inorganic acids, or combinations thereof. The base source may be sourced from any material able to increase the pH value of the system, such as organic bases, inorganic bases, organic molecules whose counter ions are anions with hydroxyl groups, or combinations thereof. The biopolymers may be sourced from the polymers generated by organisms. The solvent may be sourced from alcohol solvents. The extracting agent used in the extraction process may be sourced from aqueous solutions of solvents and acid sources.

The present invention also proposes a method for fabricating epoxide, wherein the titanium-containing silicon oxide, which is fabricated by the abovementioned method of the present invention, is used as the catalyst to enable the reaction of the olefins and oxides and generate epoxides.

In one embodiment of the present invention, a silylation method is used to increase the catalytic activity of the catalyst before the catalytic reaction.

In the abovementioned methods, the quantity of the used catalyst is not strictly limited as long as the quantity of the used catalyst is sufficient to enable the epoxidation reaction to be completed in the shortest time. The molar ratio of the olefin to the oxide, which is used in the reaction, is 1:100-100:1, preferably 1:10-10:1. The reaction temperature is not particularly limited, normally 0-200° C., preferably 25-150° C. The reaction pressure is not particularly limited as long as the pressure is higher than a pressure able to keep the reactants in the liquid state, preferably 1-100 atm. The reaction time is 1 minute-48 hours, preferably 5 minutes-8 hours.

The methods of the present invention are applicable to any reactor or device. For example, the methods of the present invention may be applied to a fixed bed reactor, a conveyor reactor, a fluidized bed reactor, a slurry agitation reactor, or a continuous stirred-tank reactor in a batch way, a continuous way, or a semi-continuous way.

The methods of the present invention are simple, low-cost, environment-friendly and thus favorable for industrial application.

Below, embodiments are described in detail to make easily understood the objectives, technical contents, characteristics, and accomplishments of the present invention.

DETAILED DESCRIPTION OF THE INVENTION

Figure 1:
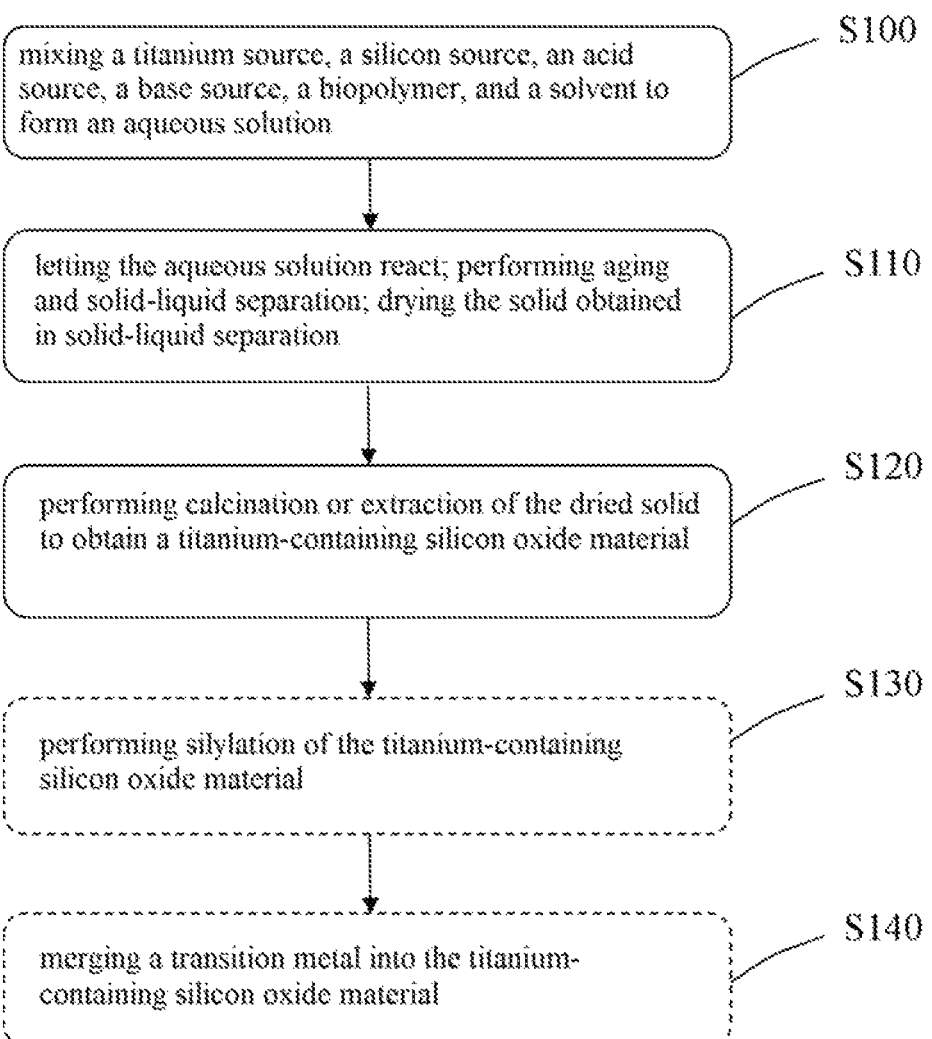
FIG. 1 shows a flowchart of a method of fabricating titanium-containing silicon oxide material according to one embodiment of the present invention.

Refer to FIG. 1 for a flowchart of a method of fabricating titanium-containing silicon oxide material according to one embodiment of the present invention. The flowchart includes 5 steps: Steps S100-S140, wherein Steps S100-S120 relates to a method of fabricating titanium-containing silicon oxide material; Step S130 and Step S140 are two steps that may be used in the fabrication process where the titanium-containing silicon oxide material with a high specific surface area is involved. In practical application, a single fabrication process may adopt one or more of Step S130 and Step S140. However, the two steps are presented on the single flowchart simultaneously for conciseness, wherein dashed-line frames are used to indicate that these steps are optional.

In Step S100, formulate a titanium source, a silicon source, an acid source and a base source, a biopolymer, and a solvent into an aqueous solution, and agitate the aqueous solution uniformly. In Step S110, place the aqueous solution at a temperature of −20-100° C. for reaction, and agitate the aqueous solution persistently for 0.5-5 hours; next, age the reactants at a temperature of 60-200° C. for 6-48 hours; next, undertake a solid-liquid separation process to separate the solid from the reaction solution; next, dry the solids separated in the solid-liquid separation process at a temperature of 30-120° C. for 0.5-6 hours persistently. In Step S120, calcine the dried solid to obtain a titanium-containing silicon oxide material with a high specific surface area; alternatively, use the mixed aqueous of a solvent and an acid source as an extracting agent to undertake an extraction process of the dried solid to obtain a titanium-containing silicon oxide material with a high specific surface area.

The titanium-containing silicon oxide material fabricated by the present invention meets the following conditions:
1. The average diameter of the pores of the titanium-containing silicon oxide material is greater than 10 Å;
2. The pores with diameters ranging from 5-200 Å have a volume of more than 90% of the total pore volume.
3. The titanium-containing silicon oxide material has a specific pore volume greater than 0.2 cm$^3$/g.

The titanium sources used by the present invention include but are not limited to be titanates, inorganic titanium sources, and combinations thereof. In details, the titanate may be selected from a group including tetramethyl titanate, tetraethyl titanate, tetra n-propyl titanate, tetra iso-propyl titanate, tetra n-butyl titanate, tetra sec-butyl titanate, tetra iso-butyl titanate, tetra tert-butyl titanate, tetra (2-ethyl-1-hexanol) titanate, tetra n-octadecane titanate and combinations thereof. The inorganic titanium sources may be titanium halides, titanium sulfate, or combinations thereof. The titanium halides may be selected from a group including titanium trichloride, titanium tetrachloride, titanium tribromide, titanium tetrabromide, titanium triiodide, and titanium tetraiodide. The abovementioned titanium sources may be used singly, or several thereof are used jointly.

The silicon sources used by the present invention include but are not limited to be amorphous silicon dioxide, alkoxysilanes, silicates, and combinations thereof. In details, the amorphous silicon dioxide has a general formula: $SiO_2$. The amorphous silicon dioxide may be but is not limited to be sourced from powder materials or bulky materials of silicon dioxide. The amorphous silicon dioxide may be but is not limited to be silica fume, white carbon, silica gel, or silica sol. The alkoxysilanes may be silanes containing 4 alkoxy groups, including tetramethylorthosilicate, tetraethylorthosilicate, tetrapropylorthosilicate, and the likes. The alkoxysilanes containing different functional groups may also be used as the silicon sources, including alkyltrialkoxysilanes, dialkyldialkoxysilanes, trialkylmonoalkoxysilanes, and the likes. The silicates may be but are not limited to be sodium silicate, potassium silicate, magnesium silicate, calcium silicate, and the likes. The abovementioned silicon sources may be used singly, or several thereof are used jointly.

The acid sources used by the present invention include but are not limited to be organic acids, inorganic acids, and any material able to decrease the pH value of the system. In details, the organic acids may be materials containing carboxyl groups or sulfonic acid groups. The organic acid sources may be selected from a group including formic acid, acetic acid, propionic acid, sulfonic acid, sulfinic acid, thionocarboxylic acids, citric acid, malic acid, tartaric acid, oxalic acid, succinic acid, lactic acid, and the likes. The inorganic acids may be materials releasing hydrogen ions and conjugate basic ions. The inorganic acids may be selected from a group including hydrochloric acid, hypochlorous acid, chlorous acid, chloric acid, perchloric acid, nitric acid, hydrazoic acid, hyponitrous acid, nitroxyl, nitrous acid, peroxynitric acid, sulfuric acid, hydrogen sulfide, hydrogen disulfide, thiosulfuric acid, sulfoxylic acid, persulfuric acid, phosphoric acid, hypophosphorous acid, phosphorous acid, metaphosphoric acid, metaphosphorous acid, diphosphonic acid, hypophosphoric acid, pyrophosphoric acid, boric acid, metaboric acid, tetraboric acid, fluoroboric acid, peroxyboric acid, carbonic acid, hydrocyanic acid, cyanic acid, fulminic acid, isocyanic acid, thiocyanic acid, isothiocyanic acid, selenocyanic acid, trithiocarbonic acid, hydrogen peroxide, hydrofluoric acid, hypofluorous acid, bromic acid, hydrobromic acid, chromic acid, dichromic acid, permanganic acid, and the likes. The abovementioned acid sources may be used singly, or several thereof are used jointly.

The base sources used by the present invention include but are not limited to be organic bases, inorganic bases, organic molecules whose counter ions are anions with hydroxyl groups, and any material able to increase the pH value of the system. In details, the organic bases may be alcohols containing alkali metals, organic metal compounds, or organic materials containing nitrogen. The organic bases may be selected from a group including sodium methoxide, potassium ethoxide, potassium tert-butoxide, butyllithium, phenyllithium, lithium diisopropylamide, lithium hexamethyldisilazide, pyridine, imidazole, benzimidazole, histidine, and the likes. The organic bases may be hydroxides containing metal ions or carbonates containing metal ions. The inorganic bases may be selected from a group including lithium hydroxide, sodium hydroxide, potassium hydroxide, magnesium hydroxide, calcium hydroxide, strontium hydroxide, barium hydroxide, aluminum hydroxide, ammonium hydroxide, zinc hydroxide, copper hydroxide, nickel hydroxide, chromium hydroxide, sodium carbonate, sodium hydrogen carbonate, potassium carbonate, potassium hydrogen carbonate, and the likes. The organic molecules whose counter ions are anions with hydroxyl groups may be trimethyloctadecylammonium hydroxide, cetyltrimethylammonium hydroxide, dodecyl trimethyl ammonium hydroxide, and the likes. The abovementioned base sources may be used singly, or several thereof are used jointly.

The biopolymers used by the present invention are polymers generated by organisms. The biopolymers may be selected from a group including chitosan, collagen, gelatin, agarose, chitin, polyhydroxyalkanoates, pullulan, starch, cellulose, hyaluronic acid, and the likes, wherein the starch includes amylose and amylopectin. The abovementioned biopolymers may be used singly, or several thereof are used jointly.

The solvents used by the present invention include but are not limited to be alcohol solvents. In details, the alcohol solvents are alcohols containing 1-10 carbon atoms. The alcohol solvents may be selected from a group including methanol, ethanol, n-propanol, isopropanol, vinyl butanol, allyl butanol, n-butanol, sec-butyl alcohol, tert-butyl alcohol, pentanol, cyclohexanol, benzyl alcohol, and diol compounds. The abovementioned solvents may be used singly, or several thereof are used jointly.

The molar ratio of the titanium source to the silicon source in the aqueous solution is 0.00001-0.5, preferably 0.0001-0.1. The weight ratio of the biopolymer to the silicon source is 0.005-5. The molar ratio of the acid source to the silicon source is 0.01-6, preferably 0.1-3. The molar ratio of the base source to the silicon source is 0.01-6, preferably 0.1-3. The weight ratio of the biopolymer to water is 0.0001-1. The weight ratio of the solvent to water is 0-5, preferably 0.01-3. The temperature of calcination is 300-800° C., preferably 450-750° C. The time of calcination is 1-9 hours, preferably 3-6 hours. The ratio of the weights of the solvent, the acid source and water in the extracting agent is 3-10: 0.01-5: 0-10, preferably 5-8: 0.05-3: 0-3. The temperature of extraction is 25-150° C., preferably 40-90° C. The time of extraction is 0.5-6 hours, preferably 1-3 hours. The weight ratio of the extracting agent to the dried solid is 1000-10.

The titanium-containing silicon oxide material may function as a catalyst. Before undertaking catalyzation, the catalyst may be silylated to decrease the number of silanol groups, as in Step S130. Thereby is decreased the intrinsic acidity of the catalyst, improved the surface characteristic of the catalyst, and enhanced the catalytic activity of the catalyst.

The silylation treatment may be performed in a gas phase method or a liquid phase method. In the gas phase method, the titanium-containing silicon oxide material reacts with a gas-phase silylation agent. In the liquid phase method, the titanium-containing silicon oxide material reacts with a liquid-phase silylation agent. The silylation treatment may be performed according to an ordinary method, using one or more kinds of organic silanes. The organic silanes for silylation may be halogenosilanes (the general formula thereof is $R^1R^2R^3SiX$), silazanes (the general formula thereof is $[R^4R^5R^6Si]_2NH$), methylsilyllimidazoles (the general formula thereof is $R^7R^8R^9Si[N_2C_3H_3]$), or methylsilyllamines (the general formula thereof is $(R^{10})_3SiN(R^{11})_2$), wherein $R^1$, $R^2$ and $R^3$ are identical or different and may be respectively a saturated alkyl group containing 1-6 carbon atoms, and a saturated phenyl group, and wherein $R^4$, $R^5$, and $R^6$ are identical or different and may be respectively an alkyl group containing 1-6 carbon atom, a haloalkyl group containing 1-6 carbon atoms, and a phenyl group, and wherein $R^7$-$R^{11}$ are respectively saturated alkyl groups containing 1-3 carbon atoms. The preferred organic silane is hexamethyldisilazane, methylsilyllamine, trimethylchlorosilane, N-trimethylformamimidazole, or a combination thereof. The solvent used in silylation may be one or more kinds of aromatic hydrocarbons containing 6-16 carbon atoms, or one or more kinds of alkanes containing 6-16 carbon atoms. The preferred solvent is toluene, benzene, isopropylbenzene-cyclohexane, or a combination thereof.

In silylation, the weight ratio of the organic silane to the titanium-containing silicon oxide material is 0.01-1, preferably 0.1-0.8; the weight ratio of the solvent to the titanium-containing silicon oxide material is 1-200, preferably 1-100; the reaction temperature of silylation is 25-200° C., preferably 50-150° C.; the reaction temperature is 0.5-3 hours, preferably 1-2 hours.

The present invention also has an alternative step (Step S140), wherein transition metals are merged into the titanium-containing silicon oxide material to enhance the catalytic activity of the material.

According to the requirement, transition metals may be merged into the titanium-containing silicon oxide material in an impregnation method, a deposition method, a blending method, or a like method. In the impregnation method, a solution of transition metals is dispersed in a suitable solvent to form a mixed solution; the mixed solution is further mixed with the titanium-containing silicon oxide material to form a titanium-containing silicon oxide material impregnated with transition metals; the titanium-containing silicon oxide material impregnated with transition metals is further dried or calcined according to requirement, wherein the concentration of the transition metals in the titanium-containing silicon oxide material is 0.001-10 wt. %, preferably 0.005-5 wt %. In the titanium-containing silicon oxide material impregnated with transition metals, transition metals are inside or outside the skeletons of the titanium-containing silicon oxide material.

In the present invention, the titanium-containing silicon oxide material may be granulated before calcination, after calcination, before extraction, after extraction, before silylation, after silylation, . . . , in any stage of the process. The granulation may be undertaken in a suitable process, such as the compression molding process or the extrusion molding process, to fabricate the titanium-containing silicon oxide material into granules having a specified range of diameters.

Because of having a high specific surface area and highly-dispersed active-titanium sites, the titanium-containing silicon oxide material fabricated by the present invention can be used as a catalyst for oxidation or selective oxidation of organic compounds. If a third group of components (such as aluminum, etc.) is added to the titanium-containing silicon oxide material fabricated by the present invention to promote the acidic positions, the titanium-containing silicon oxide material can be used to catalyze alkylation, reforming, etc.

The titanium-containing silicon oxide material fabricated by the present invention can be used to fabricate epoxide.

Figure 2:
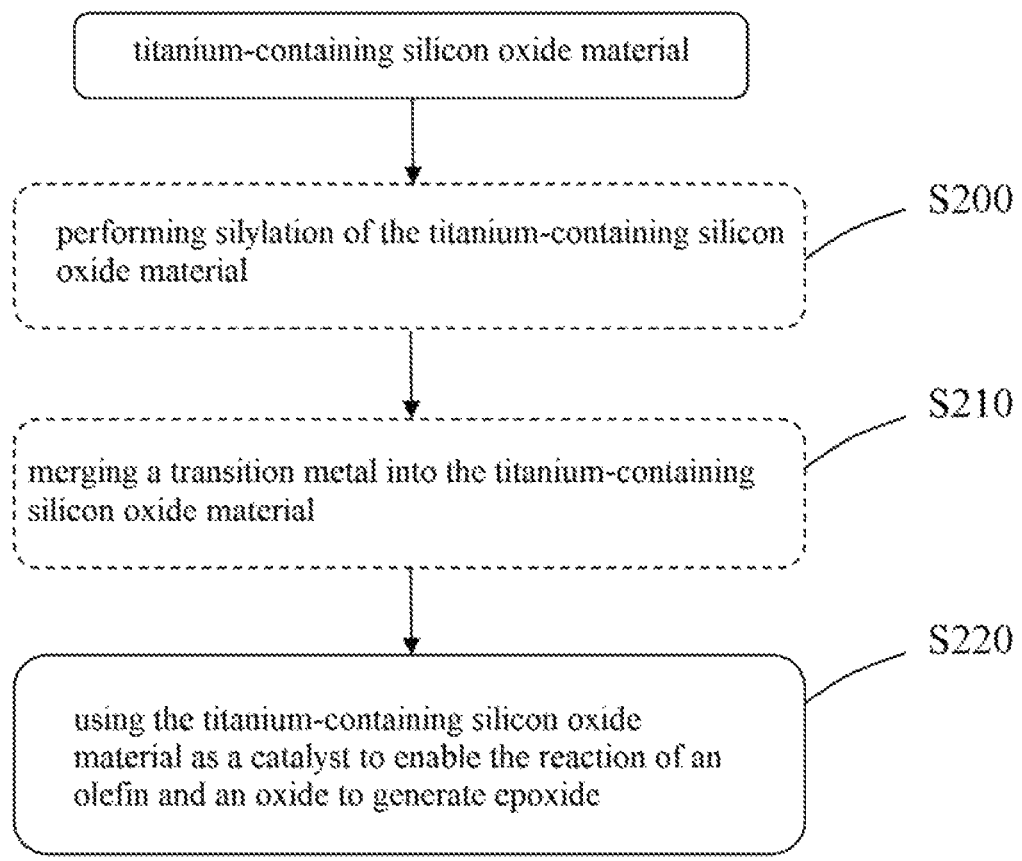
FIG. 2 shows a flowchart of using a titanium-containing silicon oxide material fabricated by the present invention can fabricate epoxide according to one embodiment of the present invention.

Refer to FIG. 2 for a flowchart of using the titanium-containing silicon oxide material fabricated by the present invention to fabricate epoxide. The flowchart includes three steps: Steps S200-S220. Step S220 describes a method for fabricating an epoxide. Step S200 and Step S210 are two steps that may be added to the process of fabricating epoxide, used to enhance the catalytic activity of the catalyst. In practical application, a single fabrication process may adopt one or more of Step S200 and Step S210. However, the two steps are presented on the single flowchart simultaneously for conciseness, wherein dashed-line frames are used to indicate that these steps are optional.

In Step S200 and Step S210, before catalytic reaction, the catalytic activity can be enhanced via silylation and/or merging transition metals into the titanium-containing silicon oxide material. The other details of these steps are similar to those of Step S130 and Step S140 and will not repeat herein. The granulation treatment may also be adopted herein.

In Step S220, the titanium-containing silicon oxide material fabricated by the present invention is used as a catalyst to catalyze the reaction of olefins and oxides to form epoxides.

The titanium-containing silicon oxide material used in the abovementioned epoxidation may be fabricated into the form of powder, lumps, microbeads, or a single bulk via extrusion-molding, compression-molding, or another method. The olefins used in the epoxidation may be but are not limited to be aliphatic compounds and cyclic compounds (including monocyclic compounds, bicyclic compounds, and polycyclic compounds). The olefins may be mono-olefins, di-olefins, and poly-olefins. While the olefin has more than two double bonds, the double bonds may be conjugated double bonds or non-conjugated double bonds. The mono-olefins may be but are not limited to be olefins containing 2-60 carbon atoms. The olefin may have a substituent, preferably a substituent stable relatively. The mono-olefins may be but are not limited to be ethylene, propylene, 1-butylene, isobutylene, 1-hexene, 2-hexene, 3-hexene, 1-octene, 1-decene, styrene, or cyclohexene. The di-olefins may be but are not limited to be butadiene or isoprene.

The oxides used in the epoxidation may be organic peroxides having a general formula: R—O—O—H, wherein R denotes a hydrocarbon group. The hydrocarbon group is a group containing 3-20 carbon atoms, preferably 3-10 carbon atoms. The hydrocarbon group may be but are not limited to be a secondary alkyl group, a tertiary alkyl group, or an aryl alkyl group, such as tertiary butyl, tertiary pentyl, cyclopentane, and 2-phenyl-2-propyl. The organic peroxide may be but is not limited to be ethylbenzene hydroperoxide, cumene hydroperoxide, tert-butyl hydroperoxide, or cyclohexyl hydroperoxide. While the hydroperoxide is cumene hydroperoxide, the product of the reaction is alpha-cumyl alcohol.

Via dehydration, alpha-cumyl alcohol is converted into alpha-methyl styrene, which has many applications in industry. Via hydrogenation, alpha-methyl styrene is converted into cumene. Via oxidization, cumene is converted into cumene hydroperoxide. The other organic peroxides also have the same recycling characteristic and thus can be used repeatedly.

The oxide used in the epoxidation may be hydrogen peroxide having a general formula: H—O—O—H. Hydrogen peroxide can be obtained from the aqueous solution thereof. The reaction of hydrogen peroxide and olefin generates epoxide and water.

The oxide used as a reactant may be a concentrated or diluted pure/impure substance.

While epoxidation is undertaken to generate epoxide, a solvent or diluent may be added to let the reaction be undertaken in a liquid state. The solvent or diluent is in the form of a liquid and inert to all the reactants and products in the epoxidation reaction. The solvent may be but is not limited to be methanol, acetone, ethylbenzene, cumene, isobutene, cyclohexane, or a combination thereof. The abovementioned solvent is a material that may exist in the oxide solution ready for use. For example, while the mixed solution of cumene hydroperoxide and cumene is used as the oxide source, cumene may function as the solvent required by the epoxidation reaction. In such a case, the addition of another type of solvent is unnecessary.

In the abovementioned methods, the amount of the used catalyst is not strictly limited as long as the epoxidation reaction can be completed in the shortest time. The molar ratio of the olefin to the oxide is 1:100-100:1, preferably 1:10-10:1. The reaction temperature is not strictly limited, normally 0-200° C., preferably 25-150° C. The reaction pressure is not strictly limited as long as the pressure is sufficient to keep all the reactants in a liquid state. The reaction pressure is preferably 1-100 atm. The reaction time is the time able to achieve the highest yield of epoxide, normally 1 minute-48 hours, preferably 5 minutes-8 hours. The methods of the present invention may be applied to a fixed bed reactor, a conveyor reactor, a fluidized bed reactor, a slurry agitation reactor, or a continuous stirred-tank reactor in a batch way, a continuous way, or a semi-continuous way.

Below, several embodiments are used to further demonstrate how the titanium-containing silicon oxide material is effectively fabricated by the present invention and how the material is used as a catalyst to catalyze the epoxidation reaction of olefin and oxide to generate epoxide.

Embodiment I

Fabrication of titanium-containing silicon oxide material: Add 2.9 kg ammonia water (28%) to a first mixture liquid containing 0.26 kg tetraisopropyl orthotitanate, 3.6 kg sodium silicate, 0.54 kg gelatin, 2.7 kg sulfuric acid (98%), 3 kg isopropanol, and 45 kg water to form a second mixture liquid; agitate the second mixture liquid at an ambient temperature for 2 hours to form a first semi-product; age the first semi-product at a temperature of 100° C. persistently for 16 hours to generate a second semi-product; filter the second semi-product to remove the solution thereof and obtain a powder; dry the powder at a temperature of 70° C.; heat the dried powder to a temperature of 550° C. at a temperature rising rate of 5° C./min and calcine the dried powder at the temperature of 750° C. persistently for 6 hours; let the powder cool down naturally and thus obtain a titanium-containing silicon oxide material with a high specific surface area. In this embodiment, more than 97% organic compounds are removed in the calcination process.

Embodiment II

Fabrication of titanium-containing silicon oxide material: The fabrication process is basically the same as that in Embodiment I except the calcination process is replaced by an extraction process. Use 10 kg sulfuric acid, 70 kg ethanol, and 20 kg water to prepare an extracting liquid. Agitate the mixture liquid containing 100 kg of the extracting liquid and 1 kg of the dried powder, which is acquired after the aging, filtering and drying processes, at a temperature of 80° C. for 2 hours to form a semi-product. Next, filter the semi-product. Next, further repeat the extraction process twice. Next, remove the solution to obtain a powder. Next, dry the powder at a temperature of 70° C. Thus, obtain a titanium-containing silicon oxide material with a high specific surface area. In this embodiment, more than 90% organic compounds are removed in the extraction process.

Embodiment III

Fabrication of propylene epoxide: Use 15 g of the titanium-containing silicon oxide material fabricated in Embodiment I as the catalyst. Mix uniformly the catalyst, 225 g cumene hydroperoxide solution (25 wt %) (the solvent thereof is cumene), and 125 g propylene in a 1-liter high-pressure airtight reactor (autoclave), and heat them to enable reaction at a temperature of 95° C. for less than 1.5 hours. The results of the reaction are shown in Table.1.

Embodiment IV

Fabrication of titanium-containing silicon oxide material: The fabrication process is basically the same as that in Embodiment I except the titanium-containing silicon oxide material with a high specific surface area, which is obtained after the calcination process, is silylated. Mix uniformly 16.5 g of the titanium-containing silicon oxide material, 165 g toluene, and 11.2 g hexamethyldisilazane; next, agitate them at a temperature of 120° C. for 1 hour; next filter and dry the product. The titanium-containing silicon oxide material obtained in this embodiment has a specific surface area of 353 m²/g, a pore volume of 0.752 ml/g and an average pore diameter of 5.5 nm.

Fabrication of propylene epoxide: The fabrication process is basically the same as that in Embodiment III except the catalyst is replaced by the titanium-containing silicon oxide material fabricated in Embodiment IV. The results of the reaction are shown in Table.1.

TABLE 1

|  | Embodiment 3 | Embodiment 4 |
| --- | --- | --- |
| Conversion rate of cumene hydroperoxide (%) (Note[1]) | 83 | 98 |
| Selectivity of propylene epoxide (%) (Note[2]) | 77 | 95 |

Note[1]:
Conversion rate of cumene hydroperoxide = Consumption of cumene hydroperoxide/Addition of cumene hydroperoxide × 100%
Note[2]:
Selectivity of propylene epoxide = Generation of propylene epoxide/Consumption of cumene hydroperoxide × 100%

Embodiment I and Embodiment II show that a calcination process or an extraction process can remove the biopolymer from the titanium-containing silicon oxide material fabricated by the present invention—a method of using biopolymer to synthesize titanium-containing silicon oxide material. According to Table.1, Embodiment III shows that the titanium-containing silicon oxide material fabricated by the present invention has a superior catalytic activity in catalyzing the epoxidation of olefins; Embodiment IV shows that silylation can significantly increase the catalytic activity of the titanium-containing silicon oxide material fabricated by the present invention in catalyzing the epoxidation of olefins.

In conclusion, the present invention proposes a method of using biopolymer to synthesize titanium-containing silicon oxide material and applications thereof, wherein the present invention uses an environment-friendly biopolymer as a templating agent to fabricate a titanium-containing silicon oxide material with a high specific surface area in an ordinary simple template method. The titanium-containing silicon oxide material fabricated by the present invention has high catalytic activity, able to function as a catalyst to successfully catalyze the epoxidation of olefins.

The embodiments described above are only to exemplify the present invention but not to limit the scope of the present invention. Any equivalent modification or variation according to the spirit of the present invention is to be also included by the scope of the present invention, which is based on the claims stated below.

What is claimed is:

1. A method for fabricating titanium-containing silicon oxide material, comprising steps:

mixing a titanium source, a silicon source, an acid source, a base source, a biopolymer, and a solvent to form an aqueous solution;

letting said aqueous solution react to form a first resultant liquid, aging said first resultant liquid to form a second resultant liquid, performing a solid-liquid separation process on said second resultant liquid, and drying a solid obtained from said solid-liquid separation process to obtain a dried solid; and performing a calcination process on said dried solid to obtain said titanium-containing silicon oxide material or performing an extraction process on said dried solid with an extracting agent to obtain said titanium-containing silicon oxide material, wherein said titanium-containing silicon oxide material meets following conditions:

pores of said titanium-containing silicon oxide material have an average diameter of greater than 10 Å;

more than 90% of total volume of said pores of said titanium-containing silicon oxide material have diameters of 5-200 Å; and said titanium-containing silicon oxide material has a specific pore volume of more than 0.2 cm³/g, wherein said biopolymer is selected from a group consisting of chitosan, collagen, gelatin, agarose, polyhydroxyalkanoates, pullulan, starch, hyaluronic acid, and combinations thereof.

2. The method for fabricating titanium-containing silicon oxide material according to claim 1, wherein said titanium source is a titanate, an inorganic titanium source, or a combination thereof; said silicon source is an amorphous silicon dioxide, an alkoxysilane, a silicate, or a combination thereof said acid source is an organic acid, an inorganic acid, or a combination thereof; said base source is an organic base, an inorganic base, an organic molecule whose counter ion is an anion with hydroxyl groups, or a combination thereof said biopolymer is a polymer generated by organisms; said solvent is an alcohol solvent; said extracting agent is a solution containing said solvent and said acid source.

3. The method for fabricating titanium-containing silicon oxide material according to claim 2, wherein said titanate is selected from a group consisting of tetramethyl titanate, tetraethyl titanate, tetra n-propyl titanate, tetra iso-propyl titanate, tetra n-butyl titanate, tetra sec-butyl titanate, tetra iso-butyl titanate, tetra tert-butyl titanate, tetra (2-ethyl-1-hexanol) titanate, tetra n-octadecane titanate and combinations thereof; said inorganic titanium source is selected from a group consisting of titanium trichloride, titanium tetrachloride, titanium tribromide, titanium tetrabromide, titanium triiodide, titanium tetraiodide, titanium sulfate, and combinations thereof.

4. The method for fabricating titanium-containing silicon oxide material according to claim 2, wherein said amorphous silicon dioxide is selected from a group consisting of silica fume, white carbon, silica gel, silica sol, and combinations thereof; said alkoxysilane is selected from a group consisting of tetramethylorthosilicate, tetraethylorthosilicate, tetrapropylorthosilicate, alkyltrialkoxysilanes, dialkyldialkoxysilanes, trialkylmonoalkoxysilanes, and combinations thereof; said silicate is selected from a group consisting of sodium silicate, potassium silicate, magnesium silicate, calcium silicate, and combinations thereof.

5. The method for fabricating titanium-containing silicon oxide material according to claim 2, wherein said organic acid is selected from a group consisting of formic acid, acetic acid, propionic acid, sulfonic acid, sulfinic acid, thionocarboxylic acids, citric acid, malic acid, tartaric acid, oxalic acid, succinic acid, lactic acid, and combinations thereof; said inorganic acid is selected from a group consisting of hydrochloric acid, hypochlorous acid, chlorous acid, chloric acid, perchloric acid, nitric acid, hydrazoic acid, hyponitrous acid, nitroxyl, nitrous acid, peroxynitric acid, sulfuric acid, hydrogen sulfide, hydrogen disulfide, thiosulfuric acid, sulfoxylic acid, persulfuric acid, phosphoric acid, hypophosphorous acid, phosphorous acid, metaphosphoric acid, metaphosphorous acid, diphosphonic acid, hypophosphoric acid, pyrophosphoric acid, boric acid, metaboric acid, tetraboric acid, fluoroboric acid, peroxyboric acid, carbonic acid, hydrocyanic acid, cyanic acid, fulminic acid, isocyanic acid, thiocyanic acid, isothiocyanic acid, selenocyanic acid, trithiocarbonic acid, hydrogen peroxide, hydrofluoric acid, hypofluorous acid, bromic acid, hydrobromic acid, chromic acid, dichromic acid, permanganic acid, and combinations thereof.

6. The method for fabricating titanium-containing silicon oxide material according to claim 2, wherein said organic base is selected from a group consisting of sodium methoxide, potassium ethoxide, potassium tert-butoxide, butyllithium, phenyllithium, lithium diisopropylamide, lithium hexamethyldisilazide, pyridine, imidazole, benzimidazole, histidine, and combinations thereof; said inorganic base is selected from a group consisting of lithium hydroxide, sodium hydroxide, potassium hydroxide, magnesium hydroxide, calcium hydroxide, strontium hydroxide, barium hydroxide, aluminum hydroxide, ammonium hydroxide, zinc hydroxide, copper hydroxide, nickel hydroxide, chromium hydroxide, sodium carbonate, sodium hydrogen carbonate, potassium carbonate, potassium hydrogen carbonate, and combinations thereof; said organic molecule whose counter ion is an anion with hydroxyl groups is selected from a group consisting of trimethyloctadecylammonium hydroxide, cetyltrimethylammonium hydroxide, dodecyl trimethyl ammonium hydroxide, and combinations thereof.

7. The method for fabricating titanium-containing silicon oxide material according to claim 2, wherein said alcohol solvent is selected from a group consisting of methanol, ethanol, n-propanol, isopropanol, vinyl butanol, allyl butanol, n-butanol, sec-butyl alcohol, tert-butyl alcohol, pentanol, cyclohexanol, benzyl alcohol, diol compounds, and combinations thereof.

8. The method for fabricating titanium-containing silicon oxide material according to claim 1, wherein a molar ratio of said titanium source to said silicon source in said aqueous solution is 0.00001-0.5; a weight ratio of said biopolymer to said silicon source is 0.005-5; a molar ratio of said acid source to said silicon source is 0.01-6; a molar ratio of said base source to said silicon source is 0.01-6; a weight ratio of said biopolymer to water is 0.0001-1; a weight ratio of said solvent to water is 0-5.

9. The method for fabricating titanium-containing silicon oxide material according to claim 8, wherein said molar ratio of said titanium source to said silicon source in said aqueous solution is 0.0001-0.1; said molar ratio of said acid source to said silicon source is 0.1-3; said molar ratio of said base source to said silicon source is 0.1-3; said weight ratio of said solvent to water is 0.01-3.

10. The method for fabricating titanium-containing silicon oxide material according to claim 1, wherein said aqueous solution reacts at a temperature ranging from −20 to 200° C. for 0.5-5 hours to form said first resultant liquid; said first resultant liquid is aged at a temperature ranging from 60 to 200° C. for 6-48 hours to form said second resultant liquid; said solid obtained from said solid-liquid separation process is dried at a temperature ranging from 30 to 120° C. for 0.5-6 hours.

11. The method for fabricating titanium-containing silicon oxide material according to claim 1, wherein a calcination temperature of said calcination process is 300-800° C.; a calcination time of said calcination process is 1-9 hours; a ratio of weights of a solvent, an acid source and water in said extracting agent used by said extraction process is 3-10: 0.01-5: 0-10; an extraction temperature of said extraction process is 25-150° C.; an extraction time of said extraction process is 0.5-6 hours; a weight ratio of said extracting agent to said dried solid is 1000-10.

12. The method for fabricating titanium-containing silicon oxide material according to claim 11, wherein said calcination temperature of said calcination process is 450-750° C.; said calcination time of said calcination process is 3-6 hours; said ratio of weights of said solvent, said acid source and water in said extracting agent used by said extraction process is 5-8: 0.05-3: 0-3; said extraction temperature of said extraction process is 40-90° C.; said extraction time of said extraction process is 1-3 hours.

13. The method for fabricating titanium-containing silicon oxide material according to claim 1 further comprising at least one of following steps:
performing a silylation treatment on said titanium-containing silicon oxide material at a reaction temperature of 25-200° C. for a reaction time of 0.5-3 hours; and
merging a transition metal into said titanium-containing silicon oxide material, wherein a concentration of said transition metal in said titanium-containing silicon oxide material is 0.001-10 wt %.

14. The method for fabricating titanium-containing silicon oxide material according to claim 13, wherein said concentration of said transition metal in said titanium-containing silicon oxide material is 0.005-5 wt %.

* * * * *